United States Patent
Iwahara et al.

(10) Patent No.: US 7,129,382 B2
(45) Date of Patent: *Oct. 31, 2006

(54) PROCESS FOR PRODUCING BISPHENOL A

(75) Inventors: Masahiro Iwahara, Yamaguchi (JP); Tetsuya Saruwatari, Yamaguchi (JP)

(73) Assignee: Idemitsu Petrochemical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/822,703

(22) Filed: Apr. 13, 2004

(65) Prior Publication Data

US 2004/0192975 A1    Sep. 30, 2004

Related U.S. Application Data

(62) Division of application No. 10/257,980, filed as application No. PCT/JP02/01654 on Feb. 25, 2002, now Pat. No. 6,740,784.

(30) Foreign Application Priority Data

Mar. 1, 2001    (JP)    ............... 2001-56471

(51) Int. Cl.
    *C07C 39/16*    (2006.01)
(52) U.S. Cl. ..................................... 568/728
(58) Field of Classification Search ............... 568/727, 568/728
    See application file for complete search history.

(56) References Cited

U.S. PATENT DOCUMENTS

| | | | |
|---|---|---|---|
| 4,308,404 A | 12/1981 | Kwantes | |
| 4,391,997 A | 7/1983 | Mendiratta | |
| 4,400,555 A | 8/1983 | Mendiratta | |
| 5,777,180 A | 7/1998 | June | |
| 5,780,690 A | 7/1998 | Berg | |
| 6,429,343 B1 | 8/2002 | Iwahara | |
| 6,586,637 B1 | 7/2003 | Iwahara | |
| 6,653,513 B1 | 11/2003 | Iwahara | |
| 6,740,784 B1 * | 5/2004 | Iwahara et al. | ............. 568/728 |
| 6,943,273 B1 * | 9/2005 | Saruwatari et al. | ......... 568/728 |

FOREIGN PATENT DOCUMENTS

| | | |
|---|---|---|
| EP | 0249102 | 12/1987 |
| EP | 0442122 | 8/1991 |
| EP | 0682004 | 11/1995 |
| EP | 0770590 | 5/1997 |
| JP | 62-148440 | 7/1987 |
| JP | 10-175898 | 6/1998 |
| JP | 10-212257 | 8/1998 |
| JP | 10-251179 | 9/1998 |
| JP | 10-251180 | 9/1998 |
| JP | 2001-335522 | 4/2001 |

* cited by examiner

*Primary Examiner*—Samuel Barts
*Assistant Examiner*—Lalitha Nagubandi
(74) *Attorney, Agent, or Firm*—Oblon, Spivak, McClelland, Maier & Neustadt, P.C.

(57) ABSTRACT

There is disclosed a process for producing bisphenol A by subjecting phenol and acetone to condensation reaction in the presence of a catalyst composed of an acid type ion exchange resin which is modified in part with a sulfur-containing amine compound, wherein the ion exchange resin having a modification rate of 10 to less than 20 mol % is used for a methanol concentration in acetone of lower than 250 ppm by weight, and the ion exchange resin having a modification rate of 20 to 65 mol % is used for a methanol concentration in acetone of 250 to 8000 ppm by weight. The above process is capable of producing bisphenol A at high conversion and selectivity by suppressing deterioration of catalytic activity due to methanol as an impurity in acetone.

6 Claims, No Drawings

PROCESS FOR PRODUCING BISPHENOL A

CROSS-REFERENCE TO RELATED APPLICATIONS

The present application is a divisional of U.S. application Ser. No. 10/257,980, filed on Oct. 29, 2002, now U.S. Pat. No. 6,740,784 which is a National Stage of International Application PCT/JP02/01654, filed on Feb. 25, 2002, which claims priority to JP 2001-56471, filed on Mar. 1, 2001.

TECHNICAL FIELD

The present invention relates to an improved process for producing bisphenol A {2,2-bis(4-hydroxyphenyl)propane}. More particularly, it pertains to a process for producing bisphenol A by subjecting phenol and acetone to condensation reaction in the presence of as a catalyst, an acid type ion exchange resin which is modified in part with a sulfur-containing amine compound, while suppressing the deterioration of catalytic activity due to methanol as an impurity in acetone to achieve a high conversion.

BACKGROUND ART

It is well-known that bisphenol A is an important compound as a starting raw material for epoxy resin or an engineering plastic such as polycarbonate resin and polyarylene resin, and accordingly it tends to increasingly expand its demand year by year.

Bisphenol A is produced by the condensation reaction of excess phenol with acetone in the presence of an acidic catalyst and as the case may be, a sulfur compound as a cocatalyst.

There has heretofore been employed an inorganic mineral acid such as sulfuric acid and hydrogen chloride as an acid catalyst to be used in the reaction. In recent years, however, attention has been paid to cationic exchange resins (refer to UK Patent GB 842209, 849565 and 883391), which have been brought into industrial applications.

On the other hand, it is known that useful sulfur compounds to be used as a cocatalyst include alkyl mercaptans with or without a substituent group such as methyl mercaptan, ethyl mercaptan and thioglycol acid ( refer to U.S. Pat. Nos. 2,359,242 and 2,775,620). The mercaptans have a function of increasing the rate of reaction and at the same time, enhancing the selectivity. For instance, in the production of bisphenol A, there are formed as a reaction by-product, 2-(2-hydroxyphenyl)-2-(4-hydroxyphenyl)-propane (o, p'-isomers) as a principal component and in addition thereto, trisphenol and polyphenol. In particular, bisphenol A, when being employed as a starting raw material for polycarbonate resin or polyarylene, is required to be minimized in contents of the above-mentioned by-products, highly pure and free from coloration. As such, the mercaptans are employed to increase the rate of reaction, suppress the formation of the by-products, and enhance the selectivity.

However, the mercaptans cause corrosion of equipment and involve environmental and sanitary problems such as odor. In recent years therefore, use is made as a catalyst, of a variety of acid type modified ion exchange resins in which a sulfur-containing group is introduced in part of its sulfonic acid group in place of the combinational use of the aforesaid cation exchange resin and mercaptans.

There is known as one of the aforesaid acid type modified ion exchange resin, an acid type ion exchange resin which is modified in part with a sulfur-containing amine compound. In the case however, where bisphenol A is produced by the condensation reaction of phenol and acetone in the presence of a catalyst composed of the foregoing acid type ion exchange resin which is modified in part with a sulfur-containing amine compound, there is brought about a problem in that the activity of the catalyst is deteriorated by methanol as an impurity in acetone. In order to solve the aforesaid problem, there is proposed a method for suppressing the deterioration of the catalyst by allowing a small amount of water to be present in the starting raw material for reaction (refer to Japanese Patent Application Laid-Open Nos. 172241/1994 (Heisei 6), 175898/1998 (Heisei 10), 251179/1998 (Heisei 10) and 251180/1998 (Heisei 10). Nevertheless, the foregoing method can not be said to be always satisfactory, since the deterioration of the catalyst is newly brought about by water, thus making it impossible to sufficiently exert the effect on suppressing the deterioration of the catalyst.

On the other hand, there is proposed a method for decreasing the content of the compound as impurities in the starting raw material to less than 0.1% by weight by subjecting the starting raw material for reaction to refining treatment, said compound being represented by the formula: R—X, wherein R is an alkyl group, an alkenyl group, a cycloalkyl group or a cycloalkenyl group, and X is OH, a halogen atom, a carboxylate group, a sulfate group or a sulfonate group. Nevertheless, the method just mentioned can not be said to be always satisfactory, since it is obliged to subject phenol and acetone as the starting raw materials to refining treatment, thereby increasing the refining steps thereof.

DISCLOSURE OF THE INVENTION

Under such circumstances, it is a general object of the present invention to provide a process for steadily producing bisphenol A in high conversion by subjecting phenol and acetone to condensation reaction in the presence of as a catalyst, an acid type ion exchange resin which is modified in part with a sulfur-containing amine compound, while suppressing the deterioration of catalytic activity due to methanol as an impurity in acetone.

Other objects of the present invention will become obvious from the text of the specification hereinafter disclosed.

In such circumstances, intensive extensive research and investigation were accumulated by the present inventors in order to achieve the above-mentioned objects. As a result, it has been found that the objects of the present invention can be achieved by using as a catalyst, an acid type ion exchange resin which is modified in part with a sulfur-containing amine compound, and which has different modification rate in accordance with the concentration of methanol in acetone as a starting raw material. The present invention has been accomplished on the basis of the foregoing findings and information.

Specifically, the present invention provides a process for producing bisphenol A by subjecting phenol and acetone to condensation reaction in the presence of, as a catalyst, an acid type ion exchange resin which is modified in part with a sulfur-containing amine compound, characterized in that the foregoing ion exchange resin having a modification rate in the range of 10 to less than 20 mol % is used for a methanol concentration in acetone of lower than 250 ppm by weight and the resin having a modification rate in the range of 20 to 65 mol % is used for a methanol concentration in acetone being in the range of 250 to 8000 ppm by weight.

BEST MODE FOR PRACTICING THE INVENTION

The process according to the present invention is that for producing bisphenol A by subjecting phenol and acetone to condensation reaction in the presence of as a catalyst, an acid type ion exchange resin which is modified in part with a sulfur-containing amine compound. The acid type ion exchange resin which is used as a base for the above-mentioned modified acid type ion exchange resin is not specifically limited, but can be selected for use from the ion exchange resins that have hitherto been customarily used as a catalyst for bisphenol A. Thus from the viewpoint of catalytic activity and the like, sulfonic acid type ion exchange resin which is strongly acidic is suitable in particular.

The foregoing sulfonic acid type ion exchange resin is not specifically limited provided that it is a strongly acidic ion exchange resin bearing a sulfonic acid group, but is exemplified by sulfonated styrene/divinyl benzene copolymer, sulfonated and crosslinked styrene polymer, phenol formaldehyde/sulfonic acid resin and benzene formaldehyde/sulfonic acid resin and the like.

On the other hand, the sulfur-containing amine compound to be used for partially modifying the acid type ion exchange resin is not specifically limited, but can be properly and optionally selected for use from previously well known compounds which can be used for modifying an acid type ion exchange resin. Examples of the above-mentioned sulfur-containing amine compound include mercaptoalkylpyridines such as 3-mercaptomethylpyridine, 3-(2-mercaptoethyl)pyridine and 4-(2-mercaptoethyl)pyridine; mercaptoalkylamines such as 2-mercaptoethylamine, 3-mercaptopropylamine and 4-mercaptobutylamine; thiazolidines such as thiazolidine, 2-2-dimethylthiazolidine, 2-methyl-2-phenylthiazolidine and 3-methylthiazolidine; and aminothiophenol such as 4-aminothiophenol. Of these are preferable 2-mercaptoethylamine and 2-2-dimethylthiazolidine. Any of these sulfur-containing amine compound may be in a free form or in the form of addition salt of an acidic substance such as hydrochloric acid or quaternary ammonium salt.

The method for partially modifying the aforesaid acid type ion exchange resin as the base by using the sulfur-containing amine compound is not specifically limited, but can be selected for use from previously well known methods.

For instance, the resin as the base can be modified by allowing an acid type ion exchange resin and a sulfur-containing amine compound to react with each other preferably in an aqueous solvent such as water so as to achieve a desirable modification rate. The reaction may be carried out at ordinary temperature or under heating. By this reaction, the sulfonic acid group as the ion exchange group reacts with the amino group in the sulfur-containing amine compound, so that the ion exchange resin is modified in part by the sulfur-containing group introduced into part of the ion exchange group.

In the process according to the present invention, use is made of modified acid type ion exchange resins each having different modification rate in accordance with the concentration of methanol in acetone as a starting raw material.

The present inventors have found the followings. In the case of using an acidic type ion exchange resin modified in part with a sulfur-containing amine compound as a condensation reaction catalyst for phenol and acetone, methanol present in acetone as an impurity reacts with the residue of the sulfur-containing amine compound in the aforesaid resin to lower the catalytic activity, but the reaction between methanol and the residue causes the sulfonic acid group in unreacted portion in the aforesaid resin to act as a catalyst, whereby a specific relationship is established between the methanol concentration and the amount of the sulfonic acid group. That is to say, in the case of a low methanol concentration, even if the sulfonic acid group in unreacted portion exists in a large amount (lower modification rate), the reaction between the methanol and the residue of the sulfur-containing amine compound is less prone to occur, thereby prolonging the service life of the modified ion exchange resin as the catalyst. On the other hand, in the case of a high methanol concentration, the service life of the catalyst can be prolonged by lessening the sulfonic acid group in unreacted portion (higher modification rate), and thereby making the reaction between the methanol and the residue of the sulfur-containing amine compound less prone to occur.

Such being the case, deterioration of catalytic activity is suppressed and the service life of the catalyst is prolonged in the present invention by setting the modification rate in the range of 10 to less than 20 mol % for a methanol concentration of lower than 250 ppm by weight in acetone as a starting raw material, and setting the modification rate in the range of 20 to 65 mol % for a methanol concentration in the range of 250 to 8000 ppm by weight therein. In the case of a methanol concentration being in the range of 700 to 8000 ppm by weight, the modification rate is preferably set in the range of 26 to 65 mol %. The modification rate, when being lower than 10 mol %, results in failure to sufficiently exhibit the effect on modification with a sulfur-containing amine compound, and in low catalytic activity irrespective of methanol concentration, whereas the modification rate, when being higher than 65 mol %, causes a decrease in free sulfonic acid group and low catalytic activity irrespective of methanol concentration.

In addition, it is possible in the present invention to use a starting raw material having a water content of approximately 500 to 5000 ppm by weight.

In general, phenol of reagent grade or for industrial use as a starting raw material has a water content of 500 to 1000 ppm by weight. Likewise, acetone as a starting raw material has a water content of 1000 to 3000 ppm by weight.

In the process according to the present invention, phenol in an excessive amount and unreacted acetone are recovered and recycled, which requires a large extent of refining in order to attain the foregoing water contents. In the reaction between phenol and acetone, water is generated in an amount equimolar with the resultant bisphenol A. For instance, the reaction between acetone and phenol in a usual molar ratio of 1:10 gives rise to a water concentration of 4000 ppm, 9000 ppm and 13000 ppm, respectively for a modification rate of 20%, 50% and 70% each. That is to say, in the case of a water content in each starting raw material being about 500 to 2000 ppm by weight, the amount of water generated by the reaction exceeds the foregoing amount, thus hardly affects the reaction performance. In fact, the addition of 0.05 to 0.2% of water hardly exhibits working effect on suppressing the influence by methanol. However, water contained in the reaction system inhibits the formation of the objective bisphenol A, and a content of 0.4% approximately in a starting raw material leads to deterioration of catalytic activity to a great extent.

By the term "modification rate" as used herein is meant a molar rate of modification of the sulfonic acid group in the acid type ion exchange resin, such modification being made by the sulfur-containing amine compound.

The ratio of phenol to acetone that are to be used in the process for producing bisphenol A according to the present invention is not specifically limited, but the amount of the unreacted acetone is preferably as small as possible in view of the easiness of refining the resultant bisphenol A, economical efficiency and the like factors. Accordingly, it is advantageous to use excess phenol over a stoichiometric amount thereof. Thus, phenol is used usually in an amount of 3 to 30 mol, preferably 5 to 20 mol per one mol of acetone. In the production of bisphenol A, a reaction solvent is unnecessary in general except for the case where the reaction liquid has unreasonably high viscosity or the reaction is conducted at such a low temperature that the operation is made difficult by solidification.

In the condensation reaction between phenol and acetone, there is usable a continuous reaction fixed-bed system in which phenol and acetone are continuously supplied and reacted in a reaction tower which is filled in with the acid type ion exchange resin modified in part with a sulfur-containing amine compound. In this case, both a single reactor and a plurality of reactors that are arranged in series or parallel are usable. For an industrial scale, it is particularly advantageous to adopt a continuous multistage reaction fixed-bed system equipped with at least two reaction towers in series each being filled in with the acid type ion exchange resin.

In the following, some description will be given of the reaction conditions of the continuous reaction fixed-bed system.

In the first place, the acetone/phenol molar ratio is selected in the range of usually 1/30 to 1/3, preferably 1/20 to 1/5. The molar ratio, when being less than 1/30, brings about a fear of an unreasonably low rate of reaction, whereas the molar ratio, when being more than 1/3, results in a tendency to form an excessive amount of impurities, and lower the selectivity to bisphenol A.

Further the reaction temperature is selected in the range of usually 40 to 150° C., preferably 55 to 100° C. The reaction temperature, when being lower than 40° C., gives rise to an unreasonably low rate of reaction and besides, extremely high viscosity of the reaction liquid, thereby causing a fear of solidification as the case may be. On the contrary, the reaction temperature, when being higher than 150° C., leads to difficulty in reaction control, deterioration of selectivity to bisphenol A(p, p'-isomer) and further decomposition or deterioration of the modified acid type ion exchange resin as the catalyst. The LHSV (liquid hourly space velocity) is selected in the range of usually 0.2 to 30 $hr^{-1}$, preferably 0.5 to 20 $hr^{-1}$.

In the process according to the present invention, the reaction mixture coming out from the reaction tower is post-treated by a well known method so that the objective bisphenol A is collected. In the following some description will be given of one example of the post-treatment. Firstly, concentration of the reaction mixture is carried out prior to crystallization. The conditions of the concentration are not specifically limited, but usually include a temperature in the range of 130 to 170° C. and a pressure in the range of 13 to 53 kPa. The temperature, when being lower than 130° C., necessitates a high degree of vacuum, whereas the temperature, when being higher than 170° C., brings about an increase in amounts of impurities or the cause for coloration of the reaction product. It is advantageous that the concentration of bisphenol A in the concentrated residual liquid ranges from 25 to 40% by weight. The concentration thereof, when being lower than 25% by weight, results in a low recovery rate of bisphenol A, whereas the concentration thereof, when being higher than 40% by weight, causes difficulty in slurry transport after crystallization.

The crystallization of bisphenol A and phenol adducts from the concentrated residual liquid is usually conducted by a vacuum cooling crystallization method which comprises cooling under reduced pressure taking advantage of the latent heat of water vaporization. In the aforesaid method, crystallization treatment is performed usually under the conditions including a temperature in the range of 40 to 70° C. and a pressure in the range of 3 to 13 kPa by adding water in an amount of 3 to 20% by weight approximately to the concentrated residual liquid. The water to be added, when being less than 3% by weight, causes insufficient heat-removal capacity, whereas the water, when being more than 20% by weight, unfavorably leads to an increase in dissolution loss of bisphenol A. Moreover, A crystallization temperature, when being lower than 40° C., gives rise to a fear of an increase in the viscosity of crystallization liquid or solidification of the same, whereas the temperature, when being higher than 70° C., unfavorably brings about an increase in dissolution loss of bisphenol A.

Subsequently, the bisphenol A and phenol adducts that have been crystallized in such a manner are separated by a well known method and thereafter are subjected to a cleaning treatment with phenol. Then the adducts that have been subjected to a cleaning treatment are separated into bisphenol A and phenol under the conditions including a temperature selected in the range of usually 130 to 200° C., preferably 150 to 180° C. and a pressure selected in the range of 3 to 20 kPa.

The residual phenol in the bisphenol A obtained by the separation treatment is removed to a substantially complete extent by steam stripping method or the like method, whereby bisphenol A with high quality is obtained.

In what follows, the present invention will be described in more detail with reference to comparative examples and working examples, which however shall never limit the present invention thereto.

EXAMPLE 1

A packed bed type reactor with an inside diameter of 12 mm and a height of 1200 mm was filled in with a sulfonic acid type ion exchange resin modified by 15 mol % with 2-mercaptoethylamine as the catalyst (manufactured by Mitsubishi Chemical Industries Ltd. under the trade name "Diaion SK-104H") in an amount of 69.3 milliliter (mL) in swelling state with water. Two sets of the reactors were connected in series.

Subsequently, phenol in a flow rate of 277 mL/Hr and acetone containing 100 ppm by weight of methanol in a flow rate of 31.2 mL/Hr were supplied to the first stage reactor to proceed with reaction at a reaction temperature maintained at 70° C.

Thus the reaction mixture was analyzed with the lapse of time, so that the conversion of phenol to bisphenol A was determined. The results are given in Table 1.

EXAMPLE 2

The procedure in Example 1 was repeated except that use was made as the catalyst, of the sulfonic acid type ion exchange resin as mentioned above but modified by 25 mol % with 2, 2-dimethylthiazolidine, and also acetone containing 650 ppm by weight of methanol.

The results are given in Table 1.

EXAMPLE 3

The procedure in Example 1 was repeated except that use was made as the catalyst, of the sulfonic acid type ion exchange resin as mentioned above but modified by 35 mol % with 2,2-dimethylthiazolidine, and also acetone containing 2000 ppm by weight of methanol.

The results are given in Table 1.

EXAMPLE 4

The procedure in Example 1 was repeated except that use was made as the catalyst, of the sulfonic acid type ion exchange resin as mentioned above but modified by 50 mol % with 2,2-dimethylthiazolidine, and also acetone containing 5000 ppm by weight of methanol.

The results are given in Table 1.

EXAMPLE 5

The procedure in Example 1 was repeated except that use was made as the catalyst, of the sulfonic acid type ion exchange resin as mentioned above but modified by 45 mol % with 2-mercaptoethylamine and also acetone containing 3000 ppm by weight of methanol.

The results are given in Table 1.

EXAMPLE 6

The procedure in Example 1 was repeated except that use was made as the catalyst, of the sulfonic acid type ion exchange resin as mentioned above but modified by 55 mol % with 2-mercaptoethylamine and also acetone containing 1000 ppm by weight of methanol.

The result is given in Table 1.

Comparative Example 1

The procedure in Example 1 was repeated except that use was made as the catalyst, of the sulfonic acid type ion exchange resin as mentioned above but modified by 15 mol % with 2,2-dimethylthiazolidine, and also acetone containing 2000 ppm by weight of methanol.

The results are given in Table 1.

Comparative Example 2

The procedure in Example 1 was repeated except that use was made as the catalyst, of the sulfonic acid type ion exchange resin as mentioned above but modified by 25 mol % with 2,2-dimethylthiazolidine, and also acetone containing 10000 ppm by weight of methanol.

The results are given in Table 1.

Comparative Example 3

The procedure in Example 1 was repeated except that use was made as the catalyst, of the sulfonic acid type ion exchange resin as mentioned above but modified by 35 mol % with 2-mercaptoethylamine and also acetone containing 15000 ppm by weight of methanol.

The results are given in Table 1.

Comparative Example 4

The procedure in Example 1 was repeated except that use was made as the catalyst, of the sulfonic acid type ion exchange resin as mentioned above but modified by 50 mol % with 2,2-dimethylthiazolidine, and also acetone containing 20000 ppm by weight of methanol.

The results are given in Table 1.

TABLE 1-1

| | Modified acid type ion exchange resin | | Concentration of methanol (ppm by weight) |
|---|---|---|---|
| | Sulfur-containing amine compound | Modification rate (mol %) | |
| Example 1 | 2-mercaptoethylamine | 15 | 100 |
| Example 2 | 2,2-dimethylthiazolidine | 25 | 650 |
| Example 3 | 2,2-dimethylthiazolidine | 35 | 2000 |
| Example 4 | 2,2-dimethylthiazolidine | 50 | 5000 |
| Comp'tive Example 1 | 2,2-dimethylthiazolidine | 15 | 2000 |
| Comp'tive Example 2 | 2,2-dimethylthiazolidine | 25 | 10000 |
| Comp'tive Example 3 | 2-mercaptoethylamine | 35 | 15000 |
| Comp'tive Example 4 | 2,2-dimethylthiazolidine | 50 | 20000 |
| Example 5 | 2-mercaptoethylamine | 45 | 3000 |
| Example 6 | 2-mercaptoethylamine | 55 | 1000 |

TABLE 1-2

| | Conversion of Phenol (%) | | | | | |
|---|---|---|---|---|---|---|
| | First Stage Reaction | | | Second Stage Reaction | | |
| | Start of Reaction | after 300 Hrs | after 600 Hrs | Start of Reaction | after 300 Hrs | after 300 Hrs |
| Example 1 | 12.2 | 10.8 | 8.7 | 15.5 | 13.7 | 11.2 |
| Example 2 | 12.5 | 11.2 | 9.9 | 15.6 | 14.2 | 13.3 |
| Example 3 | 12.1 | 10.9 | 9.4 | 15.2 | 13.8 | 13.1 |
| Example 4 | 10.9 | 8.2 | 7.1 | 14.5 | 12.5 | 11.8 |
| Comp'tive Example 1 | 12.3 | 6.2 | 4.1 | 15.6 | 8.1 | 6.3 |
| Comp'tive Example 2 | 12.3 | 6.0 | 3.7 | 15.4 | 8.3 | 4.3 |
| Comp'tive Example 3 | 12.0 | 7.2 | 3.4 | 15.0 | 10.9 | 5.2 |
| Comp'tive Example 4 | 10.6 | 6.2 | 3.9 | 14.1 | 11.0 | 6.1 |
| Example 5 | 11.5 | 10.7 | 9.5 | 14.9 | 13.7 | 13.0 |
| Example 6 | 10.5 | 8.0 | 6.9 | 13.7 | 11.8 | 11.1 |

INDUSTRIAL APPLICABILITY

According to the present invention, it is made possible to steadily produce bisphenol A in high conversion, while suppressing the deterioration of the catalyst due to methanol as an impurity in acetone by virtue of the process for producing the same by condensation reaction between phenol and acetone using an acid type ion exchange resin which is modified in part with a sulfur-containing amine compound.

The invention claimed is:

1. A process for producing bisphenol A comprising condensing phenol and acetone in the presence of, as a catalyst, an acid type of ion exchange resin which is modified in part with a sulfur-containing amine compound, wherein the ion exchange resin which has different modification rate is used in accordance with the concentration of methanol in acetone as a starting raw material and:
 (i) said condensing is performed in reaction equipment which comprises at least two reactors in series,
 (ii) said ion exchange resin has a modification rate in the range of 26 to 65 mol %,
 (iii) the methanol concentration in acetone is in the range of 700 to 8000 ppm by weight, and
 (iv) the water content of the starting raw material for condensing is maintained to be less than 0.4% by weight.

2. The process for producing bisphenol A according to claim 1, wherein said acid type ion exchange resin is strongly acidic sulfonic acid type ion exchange resin.

3. The process for producing bisphenol A according to claim 1, wherein the sulfur-containing amine compound is at least one species selected from the group consisting of mercaptoalkylpyridines, mercaptoalkylamines, thiazolidines and aminothiophenol.

4. The process for producing bisphenol A according to claim 3, wherein the mercaptoalkylamine is 2-mercaptoethylamine and the thiazolidine is 2-2-dimethylthiazolidine.

5. The process for producing bisphenol A according to claim 1, wherein molar ratio of acetone to phenol ranges from 1/30 to 1/3.

6. The process for producing bisphenol A according to claim 1, wherein the reaction temperature ranges from 40 to 150° C.

* * * * *

UNITED STATES PATENT AND TRADEMARK OFFICE
CERTIFICATE OF CORRECTION

PATENT NO.         : 7,129,382 B2
APPLICATION NO. : 10/822703
DATED              : October 31, 2006
INVENTOR(S)        : Iwahara et al.

It is certified that error appears in the above-identified patent and that said Letters Patent is hereby corrected as shown below:

On the title page, Item (73), the Assignee is incorrect. Item (73) should read:
-- (73) Assignee: Idemitsu Kosan Co., Ltd., Tokyo (JP)--

Signed and Sealed this

Sixteenth Day of October, 2007

JON W. DUDAS
*Director of the United States Patent and Trademark Office*